US005578481A

United States Patent [19]

Ishikawa

[11] Patent Number: 5,578,481
[45] Date of Patent: Nov. 26, 1996

[54] CLONING AND CHARACTERIZATION OF A CARDIAC ADENYLYL CYCLASE

[75] Inventor: Yoshihiro Ishikawa, Cresskill, N.J.

[73] Assignee: American Cyanamid Company, Wayne, N.J.

[21] Appl. No.: 240,357

[22] Filed: May 10, 1994

Related U.S. Application Data

[62] Division of Ser. No. 793,961, Nov. 18, 1991, Pat. No. 5,334,521.

[51] Int. Cl.[6] .................................................. C12N 9/88
[52] U.S. Cl. ............................................................. 435/232
[58] Field of Search ............................................. 435/232

[56] References Cited

PUBLICATIONS

Mollner et al., Eur. J. Biochem. 171:265–271 (1988).
Bakalyar et al., Science 250:1403–1406 (1990).
Pfeuffer et al., Methods in Enzymology, vol. 195, pp. 83–91 (Academic Press, Inc., N.Y. 1991).
Gao et al., Proc. Natl. Acad. Sci. USA 88:10178–10182 (1991).
Pfeuffer et al., Proc. Natl. Acad. Sci. USA 82:3086–3090 (1985).
Krupinski et al., Science 244:1558–1564 (1989).
Homcy et al., Proc. Natl. Acad. Sci. USA 75(1):59–63 (1978).
Parma et al., Biochem. Biophys. Res. Comm. 179(1):455–462 (1991).
Feinstein et al., Proc. Natl. Acad. Sci. USA 88:10173–10177 (1991).
Ishikawa et al., J. Biol. Chem. 267(19):13553–13557 (1992).
Katsushika et al., Proc. Natl. Acad. Sci. USA 89:8774–8778 (1992).
Yoshimura et al., Proc. Natl. Acad. Sci. USA 89:6716–6720 (1992).
Wayman et al., FASEB J. 6(5):A1632 (Feb. 28, 1992).

*Primary Examiner*—Robert A. Wax
*Assistant Examiner*—Keith D. Hendricks

[57] ABSTRACT

A DNA sequence encoding a novel effector enzyme referred to as a cardiac adenylyl cyclase is described. The amino acid sequence of the cardiac adenylyl cyclase encoded by that DNA sequence is also described.

1 Claim, 12 Drawing Sheets

```
     10         20         30         40         50         60
      *          *          *          *          *          *
CGGCCGGGCGGGCTGCGGGCGGCGAGGCTCGCCGGGGCGCGGGCGGCGGGGGGCGCGGGG 70         80         90        100        110        120
      *          *          *          *          *          *
CGGCCGGCCGGGCCGGAGCCCGGGGGGCGGCGGGGCGGGGTCCGGGGCGGCGCGGAGCGG 130        140        150        160        170        180
      *          *          *          *          *          *
GGCCGGCAGCATGTCGTGGTTTAGTGGCCTCCTGGTCCCCAAAGTGGATGAACGGAAGAC
            M  S  W  F  S  G  L  L  V  P  K  V  D  E  R  K  T>
               ↑
    190        200        210        220        230        240
      *          *          *          *          *          *
AGCCTGGGGTGAACGCAATGGGCAGAAGCGTCCACGCCGCGGGACTCGGACCAGTGGCTT
 A  W  G  E  R  N  G  Q  K  R  P  R  R  G  T  R  T  S  G  F>

250        260        270        280        290        300
      *          *          *          *          *          *
CTGCACGCCCCGCTATATGAGCTGCCTCCGGGATGCGCAGCCCCCCAGTCCCACCCCTGC
 C  T  P  R  Y  M  S  C  L  R  D  A  Q  P  P  S  P  T  P  A>

310        320        330        340        350        360
      *          *          *          *          *          *
GGCTCCCCCTCGGTGCCCCTGGCAGGATGAGGCCTTCATCCGGAGAGGCGGCCCGGGCAA
 A  P  P  R  C  P  W  Q  D  E  A  F  I  R  R  G  G  P  G  K>

370        380        390        400        410        420
      *          *          *          *          *          *
GGGCACGGAGCTGGGGCTGCGGGCGGTGGCCCTGGGCTTCGAGGACACTGAGGCCATGTC
 G  T  E  L  G  L  R  A  V  A  L  G  F  E  D  T  E  A  M  S>

430        440        450        460        470        480
      *          *          *          *          *          *
AGCGGTTGGGGCAGCTGGAGGTGGCCCTGACGTGACCCCCGGGAGTAGGCGATCCTGCTG
 A  V  G  A  A  G  G  G  P  D  V  T  P  G  S  R  R  S  C  W>

490        500        510        520        530        540
      *          *          *          *          *          *
GCGCCGTCTGGCCCAGGTGTTCCAGTCGAAGCAGTTCCGCTCGGCCAAGCTGGAGCGCCT
 R  R  L  A  Q  V  F  Q  S  K  Q  F  R  S  A  K  L  E  R  L>

550        560        570        580        590        600
      *          *          *          *          *          *
GTACCAGCGGTACTTCTTTCAGATGAACCAGAGCAGCCTGACGCTGCTGATGGCGGTGCT
 Y  Q  R  Y  F  F  Q  M  N  Q  S  S  L  T  L  L  M  A  V  L>
```

FIG. 2A

```
         610       620       630       640       650       660
          *         *         *         *         *         *
GGTGCTGCTGACAGCGGTGCTGCTAGCCTTCCATGCTGCACCTGCCCGCCCTCAGCCTGC
  V  L  L  T  A  V  L  L  A  F  H  A  A  P  A  R  P  Q  P  A>

670       680       690       700       710       720
          *         *         *         *         *         *
CTACGTGGCCCTGCTGGCCTGTGCCGCCACCCTCTTCGTGGCGCTCATGGTGGTGTGTAA
  Y  V  A  L  L  A  C  A  A  T  L  F  V  A  L  M  V  V  C  N>

730       740       750       760       770       780
          *         *         *         *         *         *
CCGGCACAGCTTTCGCCAGGACTCCATGTGGGTGGTGAGCTACGTGGTGCTGGGCATCCT
  R  H  S  F  R  Q  D  S  M  W  V  V  S  Y  V  V  L  G  I  L>

790       800       810       820       830       840
          *         *         *         *         *         *
GGCAGCCGTTCAGGTTGGGGGTGCCCTGGCAGCCAACCCCCGCAGCCCCTCTGTGGGCCT
  A  A  V  Q  V  G  G  A  L  A  A  N  P  R  S  P  S  V  G  L>

850       860       870       880       890       900
          *         *         *         *         *         *
CTGGTGCCCTGTGTTTTTTGTCTACATCACCTACACGCTCCTACCCATCCGCATGCGGGC
  W  C  P  V  F  F  V  Y  I  T  Y  T  L  L  P  I  R  M  R  A>

910       920       930       940       950       960
          *         *         *         *         *         *
AGCTGTCTTCAGTGGCCTGGGCCTGTCCACCCTGCATTTGATCTTGGCCTGGCAACTCAA
  A  V  F  S  G  L  G  L  S  T  L  H  L  I  L  A  W  Q  L  N>

970       980       990      1000      1010      1020
          *         *         *         *         *         *
CCGCGGTGACGCCTTCCTCTGGAAGCAGCTCGGTGCCAACATGCTGCTGTTCCTCTGCAC
  R  G  D  A  F  L  W  K  Q  L  G  A  N  M  L  L  F  L  C  T>

1030      1040      1050      1060      1070      1080
          *         *         *         *         *         *
CAACGTCATTGGCATCTGCACACACTACCCAGCTGAGGTCTCTCAGCGCCAGGCCTTTCA
  N  V  I  G  I  C  T  H  Y  P  A  E  V  S  Q  R  Q  A  F  Q>

1090      1100      1110      1120      1130      1140
          *         *         *         *         *         *
GGAGACCCGCGGTTACATTCAGGCCCGGCTGCACCTGCCAGATGAGAACCGGCAGCAGGA
  E  T  R  G  Y  I  Q  A  R  L  H  L  P  D  E  N  R  Q  Q  E>
```

FIG. 2B

```
          1150       1160       1170       1180       1190       1200
            *          *          *          *          *          *
        ACGGCTGCTGCTGTCCGTGTTGCCCCAGCATGTTGCCATGGAGATGAAAGAAGATATCAA
          R  L  L  S  V  L  P  Q  H  V  A  M  E  M  K  E  D  I  N>

1210       1220       1230       1240       1250       1260
            *          *          *          *          *          *
        CACAAAGAAAGAAGACATGATGTTCCACAAGATCTACATCCAGAAGCATGACAATGTCAG
          T  K  K  E  D  M  M  F  H  K  I  Y  I  Q  K  H  D  N  V  S>

1270       1280       1290       1300       1310       1320
            *          *          *          *          *          *
        CATCCTGTTTGCAGACATTGAAGGCTTCACCAGCCTGGCGTCCCAGTGCACCGCGCAGGA
          I  L  F  A  D  I  E  G  F  T  S  L  A  S  Q  C  T  A  Q  E>

1330       1340       1350       1360       1370       1380
            *          *          *          *          *          *
        GCTGGTCATGACCCTGAACGAGCTCTTCGCCCGGTTTGACAAGCTGGCTGCGGAAAATCA
          L  V  M  T  L  N  E  L  F  A  R  F  D  K  L  A  A  E  N  H>

1390       1400       1410       1420       1430       1440
            *          *          *          *          *          *
        CTGCCTGAGGATCAAGATCTTAGGGGACTGTTACTACTGTGTGTCGGGGCTGCCGGAGGC
          C  L  R  I  K  I  L  G  D  C  Y  Y  C  V  S  G  L  P  E  A>

1450       1460       1470       1480       1490       1500
            *          *          *          *          *          *
        CCGGGCAGACCATGCCCACTGCTGTGTGGAGATGGGGGTGGACATGATCGAGGCCATCTC
          R  A  D  H  A  H  C  C  V  E  M  G  V  D  M  I  E  A  I  S>

1510       1520       1530       1540       1550       1560
            *          *          *          *          *          *
        GCTGGTGCGTGAGGTGACAGGTGTGAACGTGAACATGCGCGTGGGCATCCACAGCGGGCG
          L  V  R  E  V  T  G  V  N  V  N  M  R  V  G  I  H  S  G  R>

1570       1580       1590       1600       1610       1620
            *          *          *          *          *          *
        TGTGCACTGTGGTGTCCTTGGCCTGCGGAAATGGCAGTTCGACGTGTGGTCCAATGACGT
          V  H  C  G  V  L  G  L  R  K  W  Q  F  D  V  W  S  N  D  V>

1630       1640       1650       1660       1670       1680
            *          *          *          *          *          *
        GACTCTGGCCAACCATATGGAGGCGGCCCGGGCCGGCCGCATCCACATCACCCGGGCCAC
          T  L  A  N  H  M  E  A  A  R  A  G  R  I  H  I  T  R  A  T>
```

FIG. 2C

```
          1690        1700        1710        1720        1730        1740
            *           *           *           *           *           *
       GCTGCAGTACCTGAACGGGGACTACGAGGTGGAGCCGGGCCGCGGTGGCGAGCGGAACGC
        L  Q  Y  L  N  G  D  Y  E  V  E  P  G  R  G  G  E  R  N  A>

1750        1760        1770        1780        1790        1800
            *           *           *           *           *           *
       GTACCTCAAGGAGCAGCACATCGAGACCTTCCTCATCCTGGGAGCCAGCCAGAAACGGAA
        Y  L  K  E  Q  H  I  E  T  F  L  I  L  G  A  S  Q  K  R  K>

1810        1820        1830        1840        1850        1860
            *           *           *           *           *           *
       AGAGGAGAAGGCCATGCTGGCCAAGCTGCAGCGGACGCGGGCCAACTCCATGGAAGGCCT
        E  E  K  A  M  L  A  K  L  Q  R  T  R  A  N  S  M  E  G  L>

1870        1880        1890        1900        1910        1920
            *           *           *           *           *           *
       GATGCCACGCTGGGTGCCCGACCGCGCCTTCTCCCGGACCAAGGACTCCAAGGCTTTCCG
        M  P  R  W  V  P  D  R  A  F  S  R  T  K  D  S  K  A  F  R>

1930        1940        1950        1960        1970        1980
            *           *           *           *           *           *
       CCAGATGGGCATTGATGATTCCAGCAAAGACAACCGGGGTGCCCAAGATGCCCTGAACCC
        Q  M  G  I  D  D  S  S  K  D  N  R  G  A  Q  D  A  L  N  P>

1990        2000        2010        2020        2030        2040
            *           *           *           *           *           *
       CGAGGATGAGGTCGATGAGTTCCTGGGCCGTGCCATCGATGCCCGCAGCATCGATCAGCT
        E  D  E  V  D  E  F  L  G  R  A  I  D  A  R  S  I  D  Q  L>

2050        2060        2070        2080        2090        2100
            *           *           *           *           *           *
       ACGGAAGGACCATGTGCGCCGCTTCCTGCTCACCTTCCAGAGAGAGGATCTTGAAAAGAA
        R  K  D  H  V  R  R  F  L  L  T  F  Q  R  E  D  L  E  K  K>

2110        2120        2130        2140        2150        2160
            *           *           *           *           *           *
       GTACTCAAGGAAGGTGGACCCCCGCTTCGGAGCCTACGTGGCCTGTGCGCTGTTGGTCTT
        Y  S  R  K  V  D  P  R  F  G  A  Y  V  A  C  A  L  L  V  F>

2170        2180        2190        2200        2210        2220
            *           *           *           *           *           *
       CTGCTTCATCTGCTTTATCCAGCTCCTCGTCTTCCCACACTCAACCGTGATGCTTGGGAT
        C  F  I  C  F  I  Q  L  L  V  F  P  H  S  T  V  M  L  G  I>
```

FIG. 2D

```
          2230        2240        2250        2260        2270        2280
            *           *           *           *           *           *
      CTACGCCAGTATCTTTGTGCTGTTGCTGATCACCGTGCTGACCTGTGCCGTGTACTCCTG
        Y   A   S   I   F   V   L   L   I   T   V   L   T   C   A   V   Y   S   C>

2290        2300        2310        2320        2330        2340
            *           *           *           *           *           *
      TGGCTCTCTCTTCCCCAAGGCCCTGCGACGTCTTTCCCGCAGCATCGTCCGCTCTCGGGC
        G   S   L   F   P   K   A   L   R   R   L   S   R   S   I   V   R   S   R   A>

2350        2360        2370        2380        2390        2400
            *           *           *           *           *           *
      ACACAGCACTGTGGTTGGCATTTTTTCAGTCTTGCTAGTGTTCACCTCTGCCATCGCCAA
        H   S   T   V   V   G   I   F   S   V   L   L   V   F   T   S   A   I   A   N>

2410        2420        2430        2440        2450        2460
            *           *           *           *           *           *
      CATGTTCACCTGTAACCACACCCCCATCCGGACCTGTGCAGCCCGGATGCTGAATGTAAC
        M   F   T   C   N   H   T   P   I   R   T   C   A   A   R   M   L   N   V   T>

2470        2480        2490        2500        2510        2520
            *           *           *           *           *           *
      ACCCGCTGACATCACTGCCTGCCACCTGCAGCAGCTCAATTACTCTCTGGGCCTGGATGC
        P   A   D   I   T   A   C   H   L   Q   Q   L   N   Y   S   L   G   L   D   A>

2530        2540        2550        2560        2570        2580
            *           *           *           *           *           *
      TCCGCTGTGTGAGGGCACCGCACCCACTTGCAGCTTCCCTGAGTACTTCGTTGGGAACAT
        P   L   C   E   G   T   A   P   T   C   S   F   P   E   Y   F   V   G   N   M>

2590        2600        2610        2620        2630        2640
            *           *           *           *           *           *
      GCTGCTGAGTCTCTTGGCCAGCTCTGTTTTCCTGCACATCAGTAGCATCGGGAAGTTGGC
        L   L   S   L   L   A   S   S   V   F   L   H   I   S   S   I   G   K   L   A>

2650        2660        2670        2680        2690        2700
            *           *           *           *           *           *
      CATGATCTTTGTCCTGGGGCTCATTTATTTGGTGCTGCTTCTGCTGGGCCCCCCCAGCAC
        M   I   F   V   L   G   L   I   Y   L   V   L   L   L   G   P   P   S   T>

2710        2720        2730        2740        2750        2760
            *           *           *           *           *           *
      CATCTTTGACAACTATGACCTGCTGCTTGGTGTCCATGGCTTGGCTTCTTCCAATGACAC
        I   F   D   N   Y   D   L   L   L   G   V   H   G   L   A   S   S   N   D   T>
```

FIG. 2E

```
       2770        2780        2790        2800        2810        2820
         *           *           *           *           *           *
CTTTGATGGGCTGGACTGCCCAGCTGCGGGGAGGGTGGCACTGAAATACATGACCCCTGT
   F  D  G  L  D  C  P  A  A  G  R  V  A  L  K  Y  M  T  P  V>

2830        2840        2850        2860        2870        2880
         *           *           *           *           *           *
GATTCTGCTGGTGTTTGCCCTGGCGCTGTATCTGCACGCCCAGCAGGTGGAATCAACTGC
   I  L  L  V  F  A  L  A  L  Y  L  H  A  Q  Q  V  E  S  T  A>

2890        2900        2910        2920        2930        2940
         *           *           *           *           *           *
ACGTCTGGACTTCCTCTGGAAACTGCAGGCAACGGGGGAGAAGGAGGAGATGGAGGAGCT
   R  L  D  F  L  W  K  L  Q  A  T  G  E  K  E  E  M  E  E  L>

2950        2960        2970        2980        2990        3000
         *           *           *           *           *           *
CCAGGCCTACAACCGAAGGCTGCTGCATAACATTCTGCCTAAGGACGTGGCTGCCCACTT
   Q  A  Y  N  R  R  L  L  H  N  I  L  P  K  D  V  A  A  H  F>

3010        3020        3030        3040        3050        3060
         *           *           *           *           *           *
CCTGGCCCGGGAGCGCCGGAACGATGAGCTCTACTACCAGTCGTGTGAGTGTGTGGCCGT
   L  A  R  E  R  R  N  D  E  L  Y  Y  Q  S  C  E  C  V  A  V>

3070        3080        3090        3100        3110        3120
         *           *           *           *           *           *
CATGTTTGCCTCCATTGCCAACTTTTCTGAGTTCTATGTGGAGCTGGAGGCAAACAATGA
   M  F  A  S  I  A  N  F  S  E  F  Y  V  E  L  E  A  N  N  E>

3130        3140        3150        3160        3170        3180
         *           *           *           *           *           *
GGGTGTCGAGTGCCTGCGGCTGCTCAACGAAATCATCGCCGACTTTGATGAGATCATCAG
   G  V  E  C  L  R  L  L  N  E  I  I  A  D  F  D  E  I  I  S>

3190        3200        3210        3220        3230        3240
         *           *           *           *           *           *
CGAGGAGCGGTTCCGGCAGCTGGAGAAAATCAAGACGATCGGTAGCACGTACATGGCTGC
   E  E  R  F  R  Q  L  E  K  I  K  T  I  G  S  T  Y  M  A  A>

3250        3260        3270        3280        3290        3300
         *           *           *           *           *           *
GTCGGGGCTGAACGCCAGCACCTACGATCAGGCCGGCCGCTCCCACATCACTGCCCTGGC
   S  G  L  N  A  S  T  Y  D  Q  A  G  R  S  H  I  T  A  L  A>
```

FIG. 2F

```
         3310        3320        3330        3340        3350        3360
           *           *           *           *           *           *
     CGACTATGCCATGCGGCTCATGGAGCAGATGAAACACATCAACGAGCACTCCTTCAACAA
      D  Y  A  M  R  L  M  E  Q  M  K  H  I  N  E  H  S  F  N  N>

3370        3380        3390        3400        3410        3420
           *           *           *           *           *           *
     CTTCCAGATGAAGATTGGGCTGAACATGGGCCCAGTTGTGGCAGGCGTCATTGGGGCTCG
       F  Q  M  K  I  G  L  N  M  G  P  V  V  A  G  V  I  G  A  R>

3430        3440        3450        3460        3470        3480
           *           *           *           *           *           *
     GAAGCCACAGTATGACATCTGGGGGAACACGGTGAATGTCTCTAGCCGTATGGACAGCAC
      K  P  Q  Y  D  I  W  G  N  T  V  N  V  S  S  R  M  D  S  T>

3490        3500        3510        3520        3530        3540
           *           *           *           *           *           *
     GGGGGGTTCCTGACCGAATCCAGGTGACCACGGACTTGTACCAGGTTCTAGCTGCCAAACG
       G  V  P  D  R  I  Q  V  T  T  D  L  Y  Q  V  L  A  A  K  R>

3550        3560        3570        3580        3590        3600
           *           *           *           *           *           *
     GTACCAGCTGGAGTGTCGAGGGGTGGTCAAGGTGAAGGGCAAGGGGGAGATGACCACCTA
       Y  Q  L  E  C  R  G  V  V  K  V  K  G  K  G  E  M  T  T  Y>

3610        3620        3630        3640        3650        3660
           *           *           *           *           *           *
     CTTCCTCAATGGGGGCCCCCCCAGTTAGCAGACGCCAGCTACAAGTTCAGCTGTCAGGAC
       F  L  N  G  G  P  P  S 3670        3680        3690        3700        3710        3720
           *           *           *           *           *           *
     CAAGGTGGGCATTTAAGTGGACTCTGTGCTCGCTGGATGGAGCTGTGGCCGGGGGCACCA 3730        3740        3750        3760        3770        3780
           *           *           *           *           *           *
     AGCCTCCAGACCCTGCTGACCACAAAAGGGAACACCTCAGCAGGCTGTGCTTGGACCATG 3790        3800        3810        3820        3830        3840
           *           *           *           *           *           *
     CTCGTCTGCCCTCAGGCTGGTGAACAAGGGATACCAAGAGGATTATGCAAGTGACTTTTA 3850        3860        3870        3880        3890        3900
           *           *           *           *           *           *
     CTTTTCTAATTGGGGTAGGGCTGGCTGTTCCCTCTTTCTTCCTGCTTTTGGGAGCAGGGG
```

FIG. 2G

```
       3910        3920        3930        3940        3950        3960
         *           *           *           *           *           *
AGGCAGCTGCAGCAGAGGCAGCAGGAGCCCTCCTGCCTGAGGGTTTAAAATGGCAGCTTG 3970        3980        3990        4000        4010        4020
         *           *           *           *           *           *
CCATGCCTACCCTTTCCCCTGTCTGTCTGGGCAACAGCATCGGGGCTGGGCCCTTCCTTT 4030        4040
         *           *
CCCTCTTTTTCCTGGGAATATTTTGT
```

FIG. 2H

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
      ( A ) LENGTH: 4046 base pairs
      ( B ) TYPE: nucleic acid
      ( C ) STRANDEDNESS: single
      ( D ) TOPOLOGY: linear ( i i ) MOLECULE TYPE: DNA (genomic)

( i x ) FEATURE:
      ( A ) NAME/KEY: CDS
      ( B ) LOCATION: 131..3625

( x i ) SEQUENCE DESCRIPTION: SEQ ID NO:1:

```
CGGCCGGGCG GGCTGCGGGC GGCGAGGCTC GCCGGGGCGC GGGCGGCGGG GGGCGCGGGG      60

CGGCCGGCCG GGCCGGAGCC CGGGGGGCGG CGGGGCGGGG TCCGGGGCGG CGCGGAGCGG     120

GGCCGGCAGC ATG TCG TGG TTT AGT GGC CTC CTG GTC CCC AAA GTG GAT       169
           Met Ser Trp Phe Ser Gly Leu Leu Val Pro Lys Val Asp
            1               5                  10

GAA CGG AAG ACA GCC TGG GGT GAA CGC AAT GGG CAG AAG CGT CCA CGC       217
Glu Arg Lys Thr Ala Trp Gly Glu Arg Asn Gly Gln Lys Arg Pro Arg
     15              20                  25

CGC GGG ACT CGG ACC AGT GGC TTC TGC ACG CCC CGC TAT ATG AGC TGC       265
Arg Gly Thr Arg Thr Ser Gly Phe Cys Thr Pro Arg Tyr Met Ser Cys
 30              35                  40                      45

CTC CGG GAT GCG CAG CCC CCC AGT CCC ACC CCT GCG GCT CCC CCT CGG       313
Leu Arg Asp Ala Gln Pro Pro Ser Pro Thr Pro Ala Ala Pro Pro Arg
                 50                  55                  60

TGC CCC TGG CAG GAT GAG GCC TTC ATC CGG AGA GGC GGC CCG GGC AAG       361
Cys Pro Trp Gln Asp Glu Ala Phe Ile Arg Arg Gly Gly Pro Gly Lys
             65                  70                  75

GGC ACG GAG CTG GGG CTG CGG GCG GTG GCC CTG GGC TTC GAG GAC ACT       409
Gly Thr Glu Leu Gly Leu Arg Ala Val Ala Leu Gly Phe Glu Asp Thr
         80                  85                  90

GAG GCC ATG TCA GCG GTT GGG GCA GCT GGA GGT GGC CCT GAC GTG ACC       457
Glu Ala Met Ser Ala Val Gly Ala Ala Gly Gly Gly Pro Asp Val Thr
     95                 100                 105

CCC GGG AGT AGG CGA TCC TGC TGG CGC CGT CTG GCC CAG GTG TTC CAG       505
Pro Gly Ser Arg Arg Ser Cys Trp Arg Arg Leu Ala Gln Val Phe Gln
110                 115                 120                 125

TCG AAG CAG TTC CGC TCG GCC AAG CTG GAG CGC CTG TAC CAG CGG TAC       553
Ser Lys Gln Phe Arg Ser Ala Lys Leu Glu Arg Leu Tyr Gln Arg Tyr
                130                 135                 140

TTC TTT CAG ATG AAC CAG AGC AGC CTG ACG CTG CTG ATG GCG GTG CTG       601
Phe Phe Gln Met Asn Gln Ser Ser Leu Thr Leu Leu Met Ala Val Leu
                145                 150                 155

GTG CTG CTG ACA GCG GTG CTG CTA GCC TTC CAT GCT GCA CCT GCC CGC       649
Val Leu Leu Thr Ala Val Leu Leu Ala Phe His Ala Ala Pro Ala Arg
            160                 165                 170

CCT CAG CCT GCC TAC GTG GCC CTG CTG GCC TGT GCC GCC ACC CTC TTC       697
Pro Gln Pro Ala Tyr Val Ala Leu Leu Ala Cys Ala Ala Thr Leu Phe
        175                 180                 185

GTG GCG CTC ATG GTG GTG TGT AAC CGG CAC AGC TTT CGC CAG GAC TCC       745
Val Ala Leu Met Val Val Cys Asn Arg His Ser Phe Arg Gln Asp Ser
190                 195                 200                 205
```

```
ATG TGG GTG GTG AGC TAC GTG GTG CTG GGC ATC CTG GCA GCC GTT CAG        793
Met Trp Val Val Ser Tyr Val Val Leu Gly Ile Leu Ala Ala Val Gln
            210                 215                 220

GTT GGG GGT GCC CTG GCA GCC AAC CCC CGC AGC CCC TCT GTG GGC CTC        841
Val Gly Gly Ala Leu Ala Ala Asn Pro Arg Ser Pro Ser Val Gly Leu
        225                 230                 235

TGG TGC CCT GTG TTT TTT GTC TAC ATC ACC TAC ACG CTC CTA CCC ATC        889
Trp Cys Pro Val Phe Phe Val Tyr Ile Thr Tyr Thr Leu Leu Pro Ile
        240                 245                 250

CGC ATG CGG GCA GCT GTC TTC AGT GGC CTG GGC CTG TCC ACC CTG CAT        937
Arg Met Arg Ala Ala Val Phe Ser Gly Leu Gly Leu Ser Thr Leu His
        255                 260                 265

TTG ATC TTG GCC TGG CAA CTC AAC CGC GGT GAC GCC TTC CTC TGG AAG        985
Leu Ile Leu Ala Trp Gln Leu Asn Arg Gly Asp Ala Phe Leu Trp Lys
270                 275                 280                 285

CAG CTC GGT GCC AAC ATG CTG CTG TTC CTC TGC ACC AAC GTC ATT GGC       1033
Gln Leu Gly Ala Asn Met Leu Leu Phe Leu Cys Thr Asn Val Ile Gly
                290                 295                 300

ATC TGC ACA CAC TAC CCA GCT GAG GTC TCT CAG CGC CAG GCC TTT CAG       1081
Ile Cys Thr His Tyr Pro Ala Glu Val Ser Gln Arg Gln Ala Phe Gln
            305                 310                 315

GAG ACC CGC GGT TAC ATT CAG GCC CGG CTG CAC CTG CCA GAT GAG AAC       1129
Glu Thr Arg Gly Tyr Ile Gln Ala Arg Leu His Leu Pro Asp Glu Asn
        320                 325                 330

CGG CAG CAG GAA CGG CTG CTG CTG TCC GTG TTG CCC CAG CAT GTT GCC       1177
Arg Gln Gln Glu Arg Leu Leu Leu Ser Val Leu Pro Gln His Val Ala
335                 340                 345

ATG GAG ATG AAA GAA GAT ATC AAC ACA AAG AAA GAA GAC ATG ATG TTC       1225
Met Glu Met Lys Glu Asp Ile Asn Thr Lys Lys Glu Asp Met Met Phe
350                 355                 360                 365

CAC AAG ATC TAC ATC CAG AAG CAT GAC AAT GTC AGC ATC CTG TTT GCA       1273
His Lys Ile Tyr Ile Gln Lys His Asp Asn Val Ser Ile Leu Phe Ala
                370                 375                 380

GAC ATT GAA GGC TTC ACC AGC CTG GCG TCC CAG TGC ACC GCG CAG GAG       1321
Asp Ile Glu Gly Phe Thr Ser Leu Ala Ser Gln Cys Thr Ala Gln Glu
            385                 390                 395

CTG GTC ATG ACC CTG AAC GAG CTC TTC GCC CGG TTT GAC AAG CTG GCT       1369
Leu Val Met Thr Leu Asn Glu Leu Phe Ala Arg Phe Asp Lys Leu Ala
        400                 405                 410

GCG GAA AAT CAC TGC CTG AGG ATC AAG ATC TTA GGG GAC TGT TAC TAC       1417
Ala Glu Asn His Cys Leu Arg Ile Lys Ile Leu Gly Asp Cys Tyr Tyr
        415                 420                 425

TGT GTG TCG GGG CTG CCG GAG GCC CGG GCA GAC CAT GCC CAC TGG TGT       1465
Cys Val Ser Gly Leu Pro Glu Ala Arg Ala Asp His Ala His Trp Cys
430                 435                 440                 445

GTG GAG ATG GGG GTG GAC ATG ATC GAG GCC ATC TCG CTG GTG CGT GAG       1513
Val Glu Met Gly Val Asp Met Ile Glu Ala Ile Ser Leu Val Arg Glu
                450                 455                 460

GTG ACA GGT GTG AAC GTG AAC ATC CGC GTG GGC ATC CAC AGC GGG CGT       1561
Val Thr Gly Val Asn Val Asn Ile Arg Val Gly Ile His Ser Gly Arg
            465                 470                 475

GTG CAC TGT GGT GTC CTT GGC CTG CGG AAA TGG CAG TTC GAC GTG TGG       1609
Val His Cys Gly Val Leu Gly Leu Arg Lys Trp Gln Phe Asp Val Trp
        480                 485                 490

TCC AAT GAC GTG ACT CTG GCC AAC CAT ATG GAG GCG GCC CGG GCC GGC       1657
Ser Asn Asp Val Thr Leu Ala Asn His Met Glu Ala Ala Arg Ala Gly
        495                 500                 505

CGC ATC CAC ATC ACC CGG GCC ACG CTG CAG TAC CTG AAC GGG GAC TAC       1705
Arg Ile His Ile Thr Arg Ala Thr Leu Gln Tyr Leu Asn Gly Asp Tyr
510                 515                 520                 525
```

-continued

| | | | | | | | | | | | | | | | | |
|---|---|---|---|---|---|---|---|---|---|---|---|---|---|---|---|---|
| GAG | GTG | GAG | CCG | GGC | CGC | GGT | GGC | GAG | CGG | AAC | GCG | TAC | CTC | AAG | GAG | 1753 |
| Glu | Val | Glu | Pro 530 | Gly | Arg | Gly | Gly | Glu | Arg 535 | Asn | Ala | Tyr | Leu | Lys 540 | Glu | |
| CAG | CAC | ATC | GAG | ACC | TTC | CTC | ATC | CTG | GGA | GCC | AGC | CAG | AAA | CGG | AAA | 1801 |
| Gln | His | Ile | Glu | Thr 545 | Phe | Leu | Ile | Leu 550 | Gly | Ala | Ser | Gln | Lys 555 | Arg | Lys | |
| GAG | GAG | AAG | GCC | ATG | CTG | GCC | AAG | CTG | CAG | CGG | ACG | CGG | GCC | AAC | TCC | 1849 |
| Glu | Glu | Lys 560 | Ala | Met | Leu | Ala | Lys 565 | Leu | Gln | Arg | Thr | Arg 570 | Ala | Asn | Ser | |
| ATG | GAA | GGC | CTG | ATG | CCA | CGC | TGG | GTG | GCC | GAC | CGC | GCC | TTC | TTC | CGG | 1897 |
| Met | Glu 575 | Gly | Leu | Met | Pro | Arg 580 | Trp | Val | Ala | Asp | Arg 585 | Ala | Phe | Phe | Arg | |
| ACC | AAG | GAC | TCC | AAG | GCT | TTC | CGC | CAG | ATG | GGC | ATT | GAT | GAT | TCC | AGC | 1945 |
| Thr 590 | Lys | Asp | Ser | Lys | Ala 595 | Phe | Arg | Gln | Met | Gly 600 | Ile | Asp | Asp | Ser | Ser 605 | |
| AAA | GAC | AAC | CGG | GGT | GCC | CAA | GAT | GCC | CTG | AAC | CCC | GAG | GAT | GAG | GTC | 1993 |
| Lys | Asp | Asn | Arg | Gly 610 | Ala | Gln | Asp | Ala | Leu 615 | Asn | Pro | Glu | Asp | Glu 620 | Val | |
| GAT | GAG | TTC | CTG | GGC | CGT | GGC | ATC | GAT | GCC | CGC | AGC | ATC | GAT | CAG | CTA | 2041 |
| Asp | Glu | Phe | Leu 625 | Gly | Arg | Gly | Ile | Asp 630 | Ala | Arg | Ser | Ile | Asp 635 | Gln | Leu | |
| CGG | AAG | GAC | CAT | GTG | CGC | CGC | TTC | CTG | CTC | ACC | TTC | CAG | AGA | GAG | GAT | 2089 |
| Arg | Lys | Asp | His 640 | Val | Arg | Arg | Phe | Leu 645 | Leu | Thr | Phe | Gln | Arg 650 | Glu | Asp | |
| CTT | GAA | AAG | AAG | TAC | TCA | AGG | AAG | GTG | GAC | CCC | CGC | TTC | GGA | GCC | TAC | 2137 |
| Leu | Glu 655 | Lys | Lys | Tyr | Ser | Arg 660 | Lys | Val | Asp | Pro | Arg 665 | Phe | Gly | Ala | Tyr | |
| GTG | GCC | TGT | GCG | CTG | TTG | GTC | TTC | TGC | TTC | ATC | TGC | TTT | ATC | CAG | CTC | 2185 |
| Val 670 | Ala | Cys | Ala | Leu | Leu 675 | Val | Phe | Cys | Phe | Ile 680 | Cys | Phe | Ile | Gln | Leu 685 | |
| CTC | GTC | TTC | CCA | CAC | TCA | ACC | GTG | ATG | CTT | GGG | ATC | TAC | GCC | AGT | ATC | 2233 |
| Leu | Val | Phe | Pro | His 690 | Ser | Thr | Val | Met | Leu 695 | Gly | Ile | Tyr | Ala | Ser 700 | Ile | |
| TTT | GTG | CTG | TTG | CTG | ATC | ACC | GTG | CTG | ACC | TGT | GCC | GTG | TAC | TCC | TGT | 2281 |
| Phe | Val | Leu | Leu 705 | Leu | Ile | Thr | Val | Leu 710 | Thr | Cys | Ala | Val | Tyr 715 | Ser | Cys | |
| GGC | TCT | CTC | TTC | CCC | AAG | GCC | CTG | CGA | CGT | CTT | TCC | CGC | AGC | ATC | GTC | 2329 |
| Gly | Ser | Leu 720 | Phe | Pro | Lys | Ala | Leu 725 | Arg | Arg | Leu | Ser | Arg 730 | Ser | Ile | Val | |
| CGC | TCT | CGG | GCA | CAC | AGC | ACT | GTG | GTT | GGC | ATT | TTT | TCA | GTC | TTG | CTA | 2377 |
| Arg | Ser 735 | Arg | Ala | His | Ser | Thr 740 | Val | Val | Gly | Ile | Phe 745 | Ser | Val | Leu | Leu | |
| GTG | TTC | ACC | TCT | GCC | ATC | GCC | AAC | ATG | TTC | ACC | TGT | AAC | CAC | ACC | CCC | 2425 |
| Val 750 | Phe | Thr | Ser | Ala | Ile 755 | Ala | Asn | Met | Phe | Thr 760 | Cys | Asn | His | Thr | Pro 765 | |
| ATC | CGG | ACC | TGT | GCA | GCC | CGG | ATG | CTG | AAT | GTA | ACA | CCC | GCT | GAC | ATC | 2473 |
| Ile | Arg | Thr | Cys | Ala 770 | Ala | Arg | Met | Leu | Asn 775 | Val | Thr | Pro | Ala | Asp 780 | Ile | |
| ACT | GCC | TGC | CAC | CTG | CAG | CAG | CTC | AAT | TAC | TCT | CTG | GGC | CTG | GAT | GCT | 2521 |
| Thr | Ala | Cys | His 785 | Leu | Gln | Gln | Leu | Asn 790 | Tyr | Ser | Leu | Gly | Leu 795 | Asp | Ala | |
| CCG | CTG | TGT | GAG | GGC | ACC | GCA | CCC | ACT | TGC | AGC | TTC | CCT | GAG | TAC | TTC | 2569 |
| Pro | Leu | Cys 800 | Glu | Gly | Thr | Ala | Pro 805 | Thr | Cys | Ser | Phe | Pro 810 | Glu | Tyr | Phe | |
| GTT | GGG | AAC | ATG | CTG | CTG | AGT | CTC | TTG | GCC | AGC | TCT | GTT | TTC | CTG | CAC | 2617 |
| Val | Gly | Asn 815 | Met | Leu | Leu | Ser | Leu 820 | Leu | Ala | Ser | Ser 825 | Val | Phe | Leu | His | |
| ATC | AGT | AGC | ATC | GGG | AAG | TTG | GCC | ATG | ATC | TTT | GTC | CTG | GGG | GTC | ATT | 2665 |
| Ile 830 | Ser | Ser | Ile | Gly | Lys 835 | Leu | Ala | Met | Ile | Phe 840 | Val | Leu | Gly | Val | Ile 845 | |

| | | | | | | | | | | | | | | | | |
|---|---|---|---|---|---|---|---|---|---|---|---|---|---|---|---|---|
| TAT | TTG | GTG | CTG | CTT | CTG | CTG | GGC | CCC | CCC | AGC | ACC | ATC | TTT | GAC | AAC | 2713 |
| Tyr | Leu | Val | Leu | Leu | Leu | Leu | Gly | Pro | Pro | Ser | Thr | Ile | Phe | Asp | Asn | |
| | | | 850 | | | | | | 855 | | | | | 860 | | |
| TAT | GAC | CTG | CTG | CTT | GGT | GTC | CAT | GGC | TTG | GCT | TCT | TCC | AAT | GAC | ACC | 2761 |
| Tyr | Asp | Leu | Leu | Leu | Gly | Val | His | Gly | Leu | Ala | Ser | Ser | Asn | Asp | Thr | |
| | | | 865 | | | | | 870 | | | | | | 875 | | |
| TTT | GAT | GGG | CTG | GAC | TGC | CCA | GCT | GCG | GGG | AGG | GTG | GCA | CTG | AAA | TAC | 2809 |
| Phe | Asp | Gly | Leu | Asp | Cys | Pro | Ala | Ala | Gly | Arg | Val | Ala | Leu | Lys | Tyr | |
| | | 880 | | | | | 885 | | | | | | 890 | | | |
| ATG | ACC | CCT | GTG | ATT | CTG | CTG | GTG | TTT | GCC | CTG | GCG | CTG | TAT | CTG | CAC | 2857 |
| Met | Thr | Pro | Val | Ile | Leu | Leu | Val | Phe | Ala | Leu | Ala | Leu | Tyr | Leu | His | |
| | | 895 | | | | | 900 | | | | | 905 | | | | |
| GCC | CAG | CAG | GTG | GAA | TCA | ACT | GCA | CGT | CTG | GAC | TTC | CTC | TGG | AAA | CTG | 2905 |
| Ala | Gln | Gln | Val | Glu | Ser | Thr | Ala | Arg | Leu | Asp | Phe | Leu | Trp | Lys | Leu | |
| 910 | | | | | 915 | | | | | 920 | | | | | 925 | |
| CAG | GCA | ACG | GGG | GAG | AAG | GAG | GAG | ATG | GAG | GAG | CTC | CAG | GCC | TAC | AAC | 2953 |
| Gln | Ala | Thr | Gly | Glu | Lys | Glu | Glu | Met | Glu | Glu | Leu | Gln | Ala | Tyr | Asn | |
| | | | | 930 | | | | | 935 | | | | | 940 | | |
| CGA | AGG | CTG | CTG | CAT | AAC | ATT | CTG | CCT | AAG | GAC | GTG | GCT | GCC | CAC | TTC | 3001 |
| Arg | Arg | Leu | Leu | His | Asn | Ile | Leu | Pro | Lys | Asp | Val | Ala | Ala | His | Phe | |
| | | | 945 | | | | | 950 | | | | | 955 | | | |
| CTG | GCC | CGG | GAG | CGC | CGG | AAC | GAT | GAG | CTC | TAC | TAC | CAG | TCG | TGT | GAG | 3049 |
| Leu | Ala | Arg | Glu | Arg | Arg | Asn | Asp | Glu | Leu | Tyr | Tyr | Gln | Ser | Cys | Glu | |
| | | 960 | | | | | 965 | | | | | 970 | | | | |
| TGT | GTG | GCC | GTC | ATG | TTT | GCC | TCC | ATT | GCC | AAC | TTT | TCT | GAG | TTC | TAT | 3097 |
| Cys | Val | Ala | Val | Met | Phe | Ala | Ser | Ile | Ala | Asn | Phe | Ser | Glu | Phe | Tyr | |
| 975 | | | | | 980 | | | | | 985 | | | | | | |
| GTG | GAG | CTG | GAG | GCA | AAC | AAT | GAG | GGT | GTC | GAG | TGC | CTG | CGG | CTG | CTC | 3145 |
| Val | Glu | Leu | Glu | Ala | Asn | Asn | Glu | Gly | Val | Glu | Cys | Leu | Arg | Leu | Leu | |
| 990 | | | | | 995 | | | | | 1000 | | | | | 1005 | |
| AAC | GAA | ATC | ATC | GCC | GAC | TTT | GAT | GAG | ATC | ATC | AGC | GAG | GAG | CGG | TTC | 3193 |
| Asn | Glu | Ile | Ile | Ala | Asp | Phe | Asp | Glu | Ile | Ile | Ser | Glu | Glu | Arg | Phe | |
| | | | 1010 | | | | | 1015 | | | | | 1020 | | | |
| CGG | CAG | CTG | GAG | AAA | ATC | AAG | ACG | ATC | GGT | AGC | ACG | TAC | ATG | GCT | GCG | 3241 |
| Arg | Gln | Leu | Glu | Lys | Ile | Lys | Thr | Ile | Gly | Ser | Thr | Tyr | Met | Ala | Ala | |
| | | | 1025 | | | | 1030 | | | | | 1035 | | | | |
| TCG | GGG | CTG | AAC | GCC | AGC | ACC | TAC | GAT | CAG | GCC | GGC | CGC | TCC | CAC | ATC | 3289 |
| Ser | Gly | Leu | Asn | Ala | Ser | Thr | Tyr | Asp | Gln | Ala | Gly | Arg | Ser | His | Ile | |
| | | | 1040 | | | | 1045 | | | | | 1050 | | | | |
| ACT | GCC | CTG | GCC | GAC | TAT | GCC | ATG | CGG | CTC | ATG | GAG | CAG | ATG | AAA | CAC | 3337 |
| Thr | Ala | Leu | Ala | Asp | Tyr | Ala | Met | Arg | Leu | Met | Glu | Gln | Met | Lys | His | |
| | | 1055 | | | | | 1060 | | | | | 1065 | | | | |
| ATC | AAC | GAG | CAC | TCC | TTC | AAC | AAC | TTC | CAG | ATG | AAG | ATT | GGG | CTG | AAC | 3385 |
| Ile | Asn | Glu | His | Ser | Phe | Asn | Asn | Phe | Gln | Met | Lys | Ile | Gly | Leu | Asn | |
| 1070 | | | | | 1075 | | | | | 1080 | | | | | 1085 | |
| ATG | GGC | CCA | GTT | GTG | GCA | GGC | GTC | ATT | GGG | GCT | CGG | AAG | CCA | CAG | TAT | 3433 |
| Met | Gly | Pro | Val | Val | Ala | Gly | Val | Ile | Gly | Ala | Arg | Lys | Pro | Gln | Tyr | |
| | | | | 1090 | | | | | 1095 | | | | | 1100 | | |
| GAC | ATC | TGG | GGG | AAC | ACG | GTG | AAT | GTC | TCT | AGC | CGT | ATG | GAC | AGC | ACG | 3481 |
| Asp | Ile | Trp | Gly | Asn | Thr | Val | Asn | Val | Ser | Ser | Arg | Met | Asp | Ser | Thr | |
| | | | 1105 | | | | | 1110 | | | | | 1115 | | | |
| GGG | GTT | CCT | GAC | CGA | ATC | CAG | GTG | ACC | ACG | GAC | TTG | TAC | CAG | GTT | CTA | 3529 |
| Gly | Val | Pro | Asp | Arg | Ile | Gln | Val | Thr | Thr | Asp | Leu | Tyr | Gln | Val | Leu | |
| | | | 1120 | | | | | 1125 | | | | | 1130 | | | |
| GCT | GCC | AAA | CGG | TAC | CAG | CTG | GAG | TGT | CGA | GGG | GTG | GTC | AAG | GTG | AAG | 3577 |
| Ala | Ala | Lys | Arg | Tyr | Gln | Leu | Glu | Cys | Arg | Gly | Val | Val | Lys | Val | Lys | |
| | | 1135 | | | | | 1140 | | | | | 1145 | | | | |
| GGC | AAG | GGG | GAG | ATG | ACC | ACC | TAC | TTC | CTC | AAT | GGG | GGC | CCC | CCC | AGT | 3625 |
| Gly | Lys | Gly | Glu | Met | Thr | Thr | Tyr | Phe | Leu | Asn | Gly | Gly | Pro | Pro | Ser | |
| 1150 | | | | | 1155 | | | | | 1160 | | | | | 1165 | |

| | | | | | |
|---|---|---|---|---|---|
| TAGCAGAGCC | CAGCTACAAG | TTCAGCTGTC | AGGACCAAGG | TGGGCATTTA | AGTGGACTCT | 3685 |
| GTGCTCGCTG | GATGGAGCTG | TGGCCGGGGG | CACCAAGCCT | CCAGACCCTG | CTGACCACAA | 3745 |
| AAGGGAACAC | CTCAGCAGGC | TGTGCTTGGA | CCATGCTCGT | CTGCCCTCAG | GCTGGTGAAC | 3805 |
| AAGGGATACC | AAGAGGATTA | TGCAAGTGAC | TTTTACTTTT | CTAATTGGGG | TAGGGCTGGC | 3865 |
| TGTTCCCTCT | TTCTTCCTGC | TTTTGGGAGC | AGGGGAGGCA | GCTGCAGCAG | AGGCAGCAGG | 3925 |
| AGCCCTCCTG | CCTGAGGGTT | TAAAATGGCA | GCTTGCCATG | CCTACCCTTT | CCCCTGTCTG | 3985 |
| TCTGGGCAAC | AGCATCGGGG | CTGGGCCCTT | CCTTTCCCTC | TTTTTCCTGG | GAATATTTTG | 4045 |
| T | | | | | | 4046 |

( 2 ) INFORMATION FOR SEQ ID NO:2:

( i ) SEQUENCE CHARACTERISTICS:
        ( A ) LENGTH: 1165 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Ser Trp Phe Ser Gly Leu Leu Val Pro Lys Val Asp Glu Arg Lys
 1               5                  10                  15

Thr Ala Trp Gly Glu Arg Asn Gly Gln Lys Arg Pro Arg Arg Gly Thr
            20                  25                  30

Arg Thr Ser Gly Phe Cys Thr Pro Arg Tyr Met Ser Cys Leu Arg Asp
        35                  40                  45

Ala Gln Pro Pro Ser Pro Thr Pro Ala Ala Pro Pro Arg Cys Pro Trp
    50                  55                  60

Gln Asp Glu Ala Phe Ile Arg Arg Gly Gly Pro Gly Lys Gly Thr Glu
65                  70                  75                  80

Leu Gly Leu Arg Ala Val Ala Leu Gly Phe Glu Asp Thr Glu Ala Met
                85                  90                  95

Ser Ala Val Gly Ala Ala Gly Gly Gly Pro Asp Val Thr Pro Gly Ser
            100                 105                 110

Arg Arg Ser Cys Trp Arg Arg Leu Ala Gln Val Phe Gln Ser Lys Gln
        115                 120                 125

Phe Arg Ser Ala Lys Leu Glu Arg Leu Tyr Gln Arg Tyr Phe Phe Gln
    130                 135                 140

Met Asn Gln Ser Ser Leu Thr Leu Leu Met Ala Val Leu Val Leu Leu
145                 150                 155                 160

Thr Ala Val Leu Leu Ala Phe His Ala Ala Pro Ala Arg Pro Gln Pro
                165                 170                 175

Ala Tyr Val Ala Leu Leu Ala Cys Ala Ala Thr Leu Phe Val Ala Leu
            180                 185                 190

Met Val Val Cys Asn Arg His Ser Phe Arg Gln Asp Ser Met Trp Val
        195                 200                 205

Val Ser Tyr Val Val Leu Gly Ile Leu Ala Ala Val Gln Val Gly Gly
    210                 215                 220

Ala Leu Ala Ala Asn Pro Arg Ser Pro Ser Val Gly Leu Trp Cys Pro
225                 230                 235                 240

Val Phe Phe Val Tyr Ile Thr Tyr Thr Leu Leu Pro Ile Arg Met Arg
                245                 250                 255

Ala Ala Val Phe Ser Gly Leu Gly Leu Ser Thr Leu His Leu Ile Leu
            260                 265                 270

Ala Trp Gln Leu Asn Arg Gly Asp Ala Phe Leu Trp Lys Gln Leu Gly
```

```
                      275                              280                              285
Ala  Asn  Met  Leu  Leu  Phe  Leu  Cys  Thr  Asn  Val  Ile  Gly  Ile  Cys  Thr
     290                      295                      300
His  Tyr  Pro  Ala  Glu  Val  Ser  Gln  Arg  Gln  Ala  Phe  Gln  Glu  Thr  Arg
305                      310                      315                           320
Gly  Tyr  Ile  Gln  Ala  Arg  Leu  His  Leu  Pro  Asp  Glu  Asn  Arg  Gln  Gln
                    325                      330                      335
Glu  Arg  Leu  Leu  Leu  Ser  Val  Leu  Pro  Gln  His  Val  Ala  Met  Glu  Met
                    340                      345                      350
Lys  Glu  Asp  Ile  Asn  Thr  Lys  Lys  Glu  Asp  Met  Met  Phe  His  Lys  Ile
                    355                      360                      365
Tyr  Ile  Gln  Lys  His  Asp  Asn  Val  Ser  Ile  Leu  Phe  Ala  Asp  Ile  Glu
     370                      375                      380
Gly  Phe  Thr  Ser  Leu  Ala  Ser  Gln  Cys  Thr  Ala  Gln  Glu  Leu  Val  Met
385                      390                      395                           400
Thr  Leu  Asn  Glu  Leu  Phe  Ala  Arg  Phe  Asp  Lys  Leu  Ala  Ala  Glu  Asn
                    405                      410                      415
His  Cys  Leu  Arg  Ile  Lys  Ile  Leu  Gly  Asp  Cys  Tyr  Tyr  Cys  Val  Ser
                    420                      425                      430
Gly  Leu  Pro  Glu  Ala  Arg  Ala  Asp  His  Ala  His  Trp  Cys  Val  Glu  Met
               435                      440                      445
Gly  Val  Asp  Met  Ile  Glu  Ala  Ile  Ser  Leu  Val  Arg  Glu  Val  Thr  Gly
     450                      455                      460
Val  Asn  Val  Asn  Ile  Arg  Val  Gly  Ile  His  Ser  Gly  Arg  Val  His  Cys
465                      470                      475                           480
Gly  Val  Leu  Gly  Leu  Arg  Lys  Trp  Gln  Phe  Asp  Val  Trp  Ser  Asn  Asp
               485                      490                      495
Val  Thr  Leu  Ala  Asn  His  Met  Glu  Ala  Ala  Arg  Ala  Gly  Arg  Ile  His
                    500                      505                      510
Ile  Thr  Arg  Ala  Thr  Leu  Gln  Tyr  Leu  Asn  Gly  Asp  Tyr  Glu  Val  Glu
          515                      520                      525
Pro  Gly  Arg  Gly  Gly  Glu  Arg  Asn  Ala  Tyr  Leu  Lys  Glu  Gln  His  Ile
     530                      535                      540
Glu  Thr  Phe  Leu  Ile  Leu  Gly  Ala  Ser  Gln  Lys  Arg  Lys  Glu  Glu  Lys
545                      550                      555                           560
Ala  Met  Leu  Ala  Lys  Leu  Gln  Arg  Thr  Arg  Ala  Asn  Ser  Met  Glu  Gly
               565                      570                      575
Leu  Met  Pro  Arg  Trp  Val  Ala  Asp  Arg  Ala  Phe  Phe  Arg  Thr  Lys  Asp
               580                      585                      590
Ser  Lys  Ala  Phe  Arg  Gln  Met  Gly  Ile  Asp  Asp  Ser  Ser  Lys  Asp  Asn
          595                      600                      605
Arg  Gly  Ala  Gln  Asp  Ala  Leu  Asn  Pro  Glu  Asp  Glu  Val  Asp  Glu  Phe
     610                      615                      620
Leu  Gly  Arg  Gly  Ile  Asp  Ala  Arg  Ser  Ile  Asp  Gln  Leu  Arg  Lys  Asp
625                      630                      635                           640
His  Val  Arg  Arg  Phe  Leu  Leu  Thr  Phe  Gln  Arg  Glu  Asp  Leu  Glu  Lys
                    645                      650                      655
Lys  Tyr  Ser  Arg  Lys  Val  Asp  Pro  Arg  Phe  Gly  Ala  Tyr  Val  Ala  Cys
               660                      665                      670
Ala  Leu  Leu  Val  Phe  Cys  Phe  Ile  Cys  Phe  Ile  Gln  Leu  Leu  Val  Phe
          675                      680                      685
Pro  His  Ser  Thr  Val  Met  Leu  Gly  Ile  Tyr  Ala  Ser  Ile  Phe  Val  Leu
     690                      695                      700
```

| | | | | | | | | | | | | | | | |
|---|---|---|---|---|---|---|---|---|---|---|---|---|---|---|---|
| Leu | Leu | Ile | Thr | Val | Leu | Thr | Cys | Ala | Val | Tyr | Ser | Cys | Gly | Ser | Leu |
| 705 | | | | | 710 | | | | 715 | | | | | | 720 |
| Phe | Pro | Lys | Ala | Leu | Arg | Arg | Leu | Ser | Arg | Ser | Ile | Val | Arg | Ser | Arg |
| | | | | 725 | | | | | 730 | | | | | 735 | |
| Ala | His | Ser | Thr | Val | Val | Gly | Ile | Phe | Ser | Val | Leu | Leu | Val | Phe | Thr |
| | | | 740 | | | | | 745 | | | | | | 750 | |
| Ser | Ala | Ile | Ala | Asn | Met | Phe | Thr | Cys | Asn | His | Thr | Pro | Ile | Arg | Thr |
| | | | 755 | | | | 760 | | | | | 765 | | | |
| Cys | Ala | Ala | Arg | Met | Leu | Asn | Val | Thr | Pro | Ala | Asp | Ile | Thr | Ala | Cys |
| | 770 | | | | | 775 | | | | | 780 | | | | |
| His | Leu | Gln | Gln | Leu | Asn | Tyr | Ser | Leu | Gly | Leu | Asp | Ala | Pro | Leu | Cys |
| 785 | | | | | 790 | | | | 795 | | | | | | 800 |
| Glu | Gly | Thr | Ala | Pro | Thr | Cys | Ser | Phe | Pro | Glu | Tyr | Phe | Val | Gly | Asn |
| | | | | 805 | | | | | 810 | | | | | 815 | |
| Met | Leu | Leu | Ser | Leu | Leu | Ala | Ser | Ser | Val | Phe | Leu | His | Ile | Ser | Ser |
| | | | 820 | | | | | 825 | | | | | 830 | | |
| Ile | Gly | Lys | Leu | Ala | Met | Ile | Phe | Val | Leu | Gly | Val | Ile | Tyr | Leu | Val |
| | | 835 | | | | | 840 | | | | | 845 | | | |
| Leu | Leu | Leu | Leu | Gly | Pro | Pro | Ser | Thr | Ile | Phe | Asp | Asn | Tyr | Asp | Leu |
| 850 | | | | | 855 | | | | | 860 | | | | | |
| Leu | Leu | Gly | Val | His | Gly | Leu | Ala | Ser | Ser | Asn | Asp | Thr | Phe | Asp | Gly |
| 865 | | | | | 870 | | | | | 875 | | | | | 880 |
| Leu | Asp | Cys | Pro | Ala | Ala | Gly | Arg | Val | Ala | Leu | Lys | Tyr | Met | Thr | Pro |
| | | | | 885 | | | | | 890 | | | | | 895 | |
| Val | Ile | Leu | Leu | Val | Phe | Ala | Leu | Ala | Leu | Tyr | Leu | His | Ala | Gln | Gln |
| | | | 900 | | | | | 905 | | | | | 910 | | |
| Val | Glu | Ser | Thr | Ala | Arg | Leu | Asp | Phe | Leu | Trp | Lys | Leu | Gln | Ala | Thr |
| | | 915 | | | | | 920 | | | | | 925 | | | |
| Gly | Glu | Lys | Glu | Glu | Met | Glu | Glu | Leu | Gln | Ala | Tyr | Asn | Arg | Arg | Leu |
| | 930 | | | | | 935 | | | | | 940 | | | | |
| Leu | His | Asn | Ile | Leu | Pro | Lys | Asp | Val | Ala | Ala | His | Phe | Leu | Ala | Arg |
| 945 | | | | | 950 | | | | | 955 | | | | | 960 |
| Glu | Arg | Arg | Asn | Asp | Glu | Leu | Tyr | Tyr | Gln | Ser | Cys | Glu | Cys | Val | Ala |
| | | | | 965 | | | | | 970 | | | | | 975 | |
| Val | Met | Phe | Ala | Ser | Ile | Ala | Asn | Phe | Ser | Glu | Phe | Tyr | Val | Glu | Leu |
| | | | 980 | | | | | 985 | | | | | 990 | | |
| Glu | Ala | Asn | Asn | Glu | Gly | Val | Glu | Cys | Leu | Arg | Leu | Leu | Asn | Glu | Ile |
| | | | 995 | | | | | 1000 | | | | | 1005 | | |
| Ile | Ala | Asp | Phe | Asp | Glu | Ile | Ile | Ser | Glu | Glu | Arg | Phe | Arg | Gln | Leu |
| | | | 1010 | | | | | 1015 | | | | | 1020 | | |
| Glu | Lys | Ile | Lys | Thr | Ile | Gly | Ser | Thr | Tyr | Met | Ala | Ala | Ser | Gly | Leu |
| 1025 | | | | | 1030 | | | | | 1035 | | | | | 1040 |
| Asn | Ala | Ser | Thr | Tyr | Asp | Gln | Ala | Gly | Arg | Ser | His | Ile | Thr | Ala | Leu |
| | | | | 1045 | | | | | 1050 | | | | | 1055 | |
| Ala | Asp | Tyr | Ala | Met | Arg | Leu | Met | Glu | Gln | Met | Lys | His | Ile | Asn | Glu |
| | | | | 1060 | | | | | 1065 | | | | | 1070 | |
| His | Ser | Phe | Asn | Asn | Phe | Gln | Met | Lys | Ile | Gly | Leu | Asn | Met | Gly | Pro |
| | | | 1075 | | | | | 1080 | | | | | 1085 | | |
| Val | Val | Ala | Gly | Val | Ile | Gly | Ala | Arg | Lys | Pro | Gln | Tyr | Asp | Ile | Trp |
| | | | 1090 | | | | | 1095 | | | | | 1100 | | |
| Gly | Asn | Thr | Val | Asn | Val | Ser | Ser | Arg | Met | Asp | Ser | Thr | Gly | Val | Pro |
| 1105 | | | | | 1110 | | | | | 1115 | | | | | 1120 |
| Asp | Arg | Ile | Gln | Val | Thr | Thr | Asp | Leu | Tyr | Gln | Val | Leu | Ala | Ala | Lys |
| | | | | 1125 | | | | | 1130 | | | | | 1135 | |

-continued

Arg Tyr Gln Leu Glu Cys Arg Gly Val Val Lys Val Lys Gly Lys Gly
            1140              1145                  1150

Glu Met Thr Thr Tyr Phe Leu Asn Gly Gly Pro Pro Ser
        1155              1160            1165

CLONING AND CHARACTERIZATION OF A CARDIAC ADENYLYL CYCLASE

This is a division of copending application Ser. No. 07/793,961, filed on Nov. 18, 1991, now U.S. Pat. No. 5,334,521.

FIELD OF THE INVENTION

This invention relates to a DNA sequence encoding a novel effector enzyme referred to as a cardiac adenylyl cyclase. This invention also relates to the amino acid sequence of the cardiac adenylyl cyclase encoded by that DNA sequence.

BACKGROUND OF THE INVENTION

The signal transduction pathway may be subdivided into three steps. The first is the recognition of the ligand by the receptor. The second is the transmission and amplification of the signal by a "transducer" protein. The final step is the generation of the second messenger by an effector enzyme.

Adenylyl cyclases are effector enzymes that are coupled to various hormone-receptor systems, such as catecholamine and ACTH. The catecholamine receptor and its transducer protein (G-protein) have been well characterized since the cloning of their cDNAs. However, relatively little is known about the adenylyl cyclase.

Once such a hormone binds to the receptor, it activates G protein, a heterotrimeric guanine nucleotide-binding regulatory protein ($\alpha$, $\beta$, $\gamma$). The activated G-protein elicits the exchange of GDP for GTP, as well as the dissociation from $\beta\gamma$ subunits. The GTP bound form of the $\alpha$-subunit stimulates adenylyl cyclase, which generates cyclic AMP from ATP. Cyclic AMP, a second messenger, activates various proteins, including protein kinases.

Protein kinases then phosphorylate other proteins, thus initiating a signal transduction cascade. Another type of activation is through the increased intracellular calcium concentration, especially in nervous tissues. After depolarization, the influx of calcium elicits the activation of calmodulin, an intracellular calcium binding protein. The activated calmodulin has been shown to bind and activate an adenylyl cyclase directly (Bibliography 1).

Several papers have suggested the diversity of the adenylyl cyclases. Using forskolin-bound affinity chromatography, a single class of the enzyme protein was purified from bovine brain (2,3). The monoclonal antibody raised against this purified protein also recognized another form of protein in the brain, which was different in size. Biochemical characteristics have shown that these two are different types of adenylyl cyclase; one is calmoduline-sensitive (CaM-sensitive) and the other is CaM-insensitive. This study (2) showed that there are two types of adenylyl cyclase in one tissue, and that these types share the same domain that could be recognized by the same antibody.

Another paper has presented genetic evidence of the diversity of adenylyl cyclase (4). An X-linked recessive mutation in Drosophilla which blocked associative learning lacked the CaM-sensitivity of adenylyl cyclase, but did possess the reactivity to fluoride or GTP. This suggests that the CaM-sensitive cyclase gene is located in the X-chromosome, which is distinct from the CaM-insensitive adenylyl cyclase gene.

Three different cDNAs have been cloned from mammalian tissues so far. These have been designated type I (brain type (5)); II (lung type (6)); and III (olfactory type (7)). The cDNA sequences of Types I and III have been published. The adenylyl cyclases coded for by these cDNAs are large proteins more than 1000 amino acids in length. Topographically, all types are similar. All have two six-transmembrane domains associated with a large cytoplasmic loop. The amino acid sequence of the cytoplasmic loop is conserved among different types of cyclase.

Tissue distribution of these adenylyl cyclase messages is well distinguished, as shown in Northern blotting studies. Type I is expressed only in the brain, type II is distributed in lung and brain, and type III is expressed mostly in the olfactory tissue with little expression in the brain. Thus, the adenylyl cyclases are distributed in a rather tissue specific manner. Despite the fact that heart tissue was one of the tissues in which adenylyl cyclase was originally identified, none of the three known types has been shown to be expressed in heart tissue.

It has been documented that a form of adenylyl cyclase is also present in the heart (8), and that the cyclase from the heart is recognized by a monoclonal antibody originally raised against the cyclase from the brain (9). Given that the three cloned types of adenylyl cyclase have a conserved amino acid sequence in their large cytoplasmic loop, the cyclase from the heart may share sequence homology in this region. Thus, it is possible to attempt to obtain an adenylyl cyclase clone from the heart by using an adenylyl cyclase cDNA from the brain. However, no adenylyl cyclase has been reported to have been cloned from cardiac tissue or expressed.

SUMMARY OF THE INVENTION

The starting point of this invention is the hypothesis that any adenylyl cyclase in the heart should share significant homology with that from the brain, and that it could be screened using a probe from the cyclase of the brain. The adenylyl cyclase in the heart has been shown to be related with the development of heart failure (10). This suggests it is involved with cardiac function.

According to this invention, a novel type of adenylyl cyclase cDNA is cloned from a canine heart library. This novel adenylyl cyclase is referred to as cardiac adenylyl cyclase (B form). This cardiac adenylyl cyclase is composed of 1165 amino acids. Another form (A form) of cardiac adenylyl cyclase, composed of 1019 amino acids, is the subject of co-pending, commonly-assigned application Ser. No. 07/751,460, filed Aug. 29, 1991.

This B form of cardiac adenylyl cyclase is expressed predominantly in the heart, as well as in the brain, but to a lesser degree in other tissues.

The B form of cyclase is translated from the cDNA in a transient expression system using CMT cells. CMT is a monkey kidney cell line stably transformed with a T-antigen gene driven by the metallothionein promoter. This cyclase is stimulated by forskolin, which is known to stimulate adenylyl cyclase activity in the heart (10).

The structure of this B form of cardiac adenylyl cyclase is similar to those of other types of adenylyl cyclase. It contains the motif of 6-transmembrane spanning regions associated with a large cytoplasmic loop. The overall homology of the amino acid sequences of the A and B forms of cardiac adenylyl cyclases is 64%. Their amino acid sequences are more homologous in the cytoplasmic portions than in the transmembrane portions. The B form of cardiac adenylyl cyclase may be involved in the regulation of cardiac function. Unless otherwise stated, the balance of this application is directed to the B form of cyclase; the A form is described in the co-pending application referred to above.

Panel A depicts a partial restriction map of adenylyl cyclase cDNA. The coding portion is boxed and a hatched box shows the polyadenylation site. N stands for NarI restriction site, S for SphI, SS for SspI and P for PstI; ATG, a translation initiation codon, and TAG, a translation termination codon are shown.

Panel B depicts two cDNA clones, numbered 6 and 27, obtained from the canine heart λgt 10 library.

FIG. 2 depicts the DNA and predicted amino acid sequence of the cardiac adenylyl cyclase. The entire coding sequence, as well as portions of the 5' and 3' untranslated sequences, are shown. The whole sequence is done bidirectionally twice by dideoxy sequencing method using either Sequanase or Taq polymerase. An arrow shows the possible translation initiation site (ATG) in an open reading frame. This ATG is accompanied by the most conserved Kozak consensus sequence.

Figure 3:
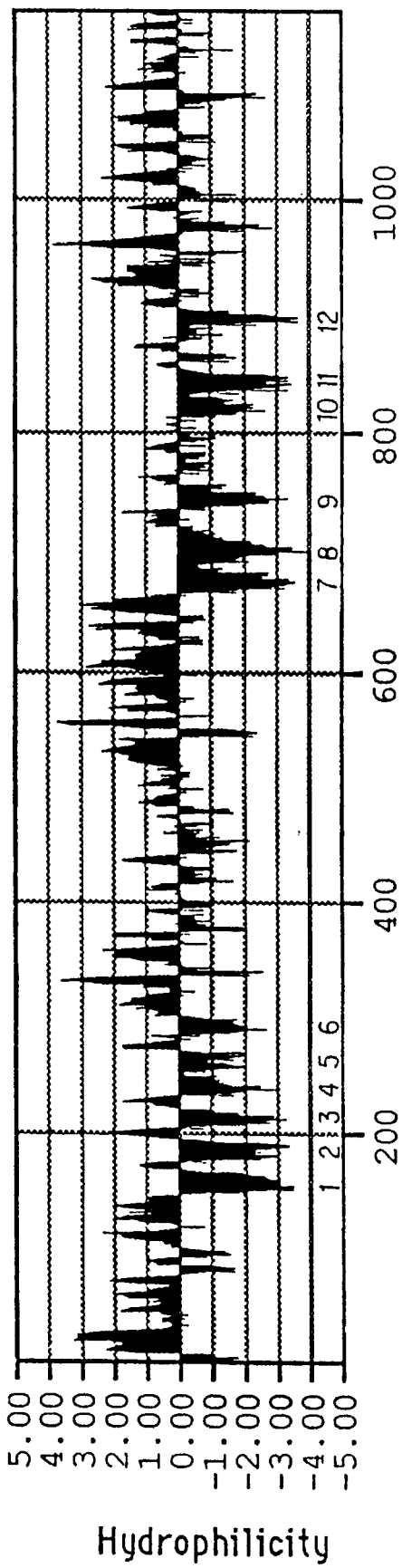

FIG. 3 depicts a hydropathy plot of the cardiac adenylyl cyclase. MacVector 3.5 software is used to analyze the membrane related structure of cardiac adenylyl cyclase. The method of Kyte and Doolittle (11) is used with a window size of 7.

Figure 4:
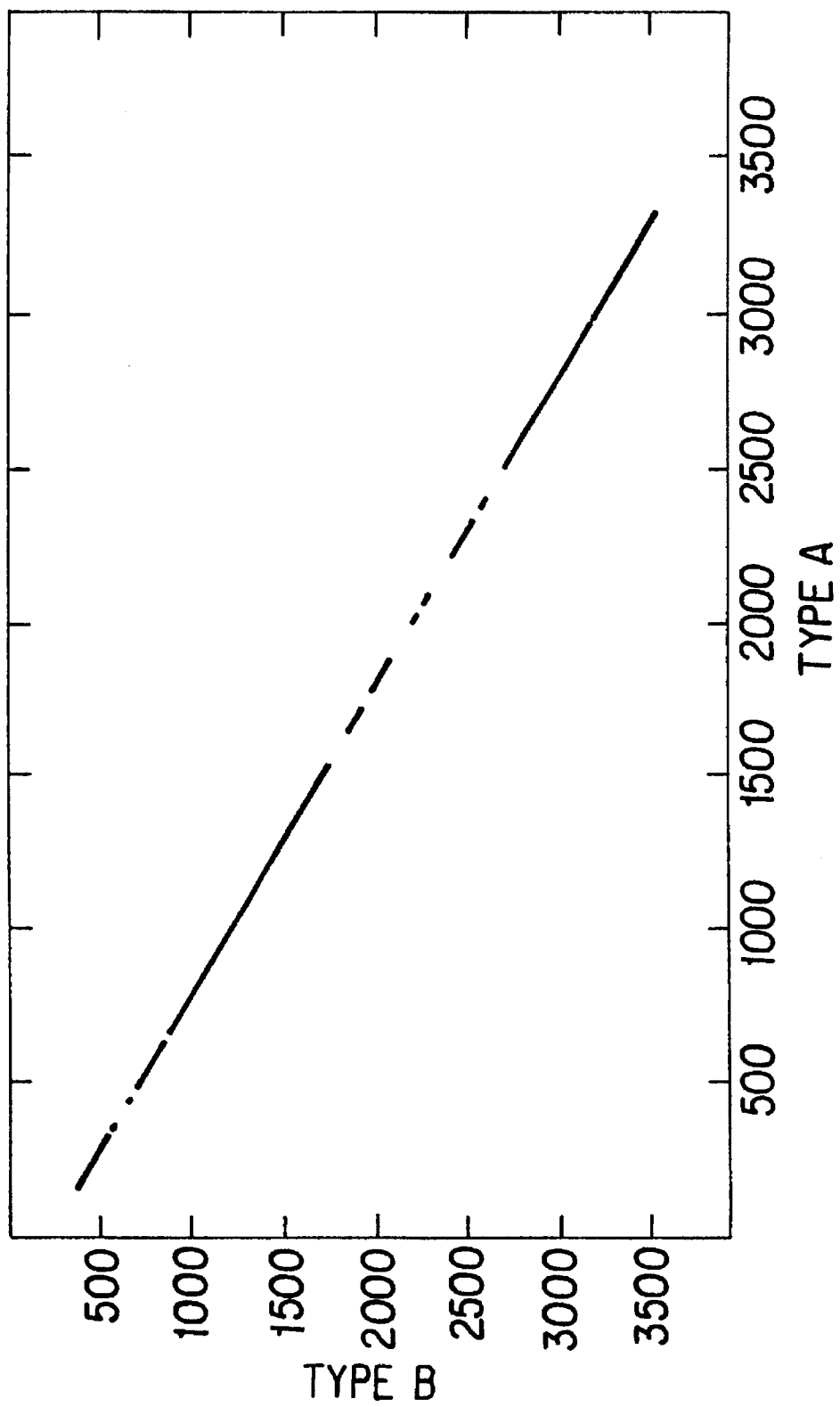

FIG. 4 depicts a DNA dot matrix comparison between the A and B forms of cardiac adenylyl cyclase. MacVector 3.0 software is used for the analysis with a stringency of 65% and a window size of 8.

Figure 5:
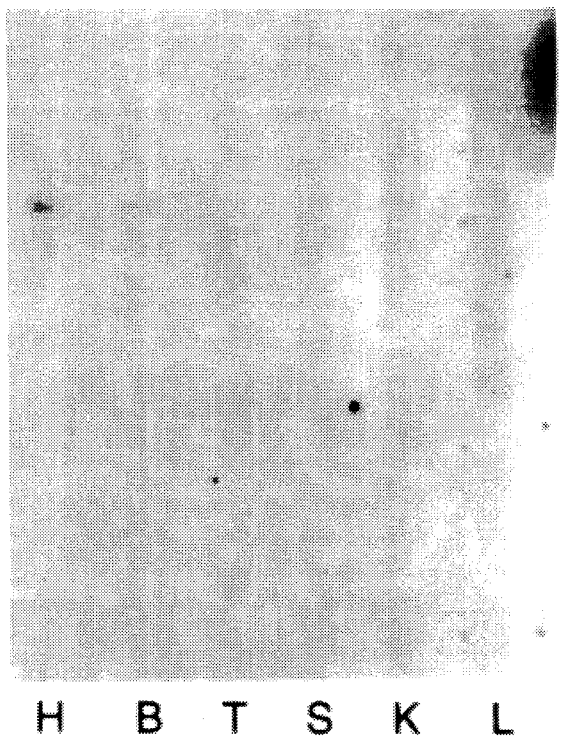

FIG. 5 depicts Northern blot analysis of various canine tissues by a fragment from cardiac adenylyl cyclase cDNA. The lanes are as follows: H-heart, B-brain, T-testis, S-skeletal muscle, K-kidney, L-lung. Standards in kilobases (kb) are at the left of the blot.

DETAILED DESCRIPTION OF THE INVENTION

The strategy used to identify and isolate the novel cardiac adenylyl cyclase begins with the construction and screening of canine heart cDNA library.

Left ventricular tissue of canine heart is used as a source of mRNA. The library is prepared in a λgt10 phage with an oligo-dT primer as described (12). The primary screening of the λgt10 library is carried out with gentle washing (less stringent conditions). Approximately $2 \times 10^6$ plaques are initially screened from the library. Prehybridization is carried out for at least two hours in a solution containing 30% formamide, 5×SSC, 5×Denhardt's, 25 mM NaPO$_4$ (pH 6.5), 0.25 mg/ml calf thymus DNA, and 0.1% sodium dodecyl sulfate (SDS) at 42° C. Hybridization is then performed in the same solution at 42° C. An 970 base pair (bp) AatI-HincII fragment from type I adenylyl cyclase cDNA is used as a probe. This fragment encodes the first cytoplasmic domain of the adenylyl cyclase, which has significant homology to other previously-known types of adenylyl cyclase (7).

The probe is radiolabelled with $^{32}$P-dCTP by the multiprimer-random labelling method. After hybridization for 18 hours, the blot is washed under increasingly stringent conditions and then radioautographed. One positive clone is obtained. The size of the insert in the clone is 5.4 kb (kilobases).

The next step is to ascertain the full length cDNA sequence from the inserts in the clones. All the positive clones from the canine heart library are subcloned into plasmid pUC18. After restriction maps are made, they are further subcloned and sequenced with universal primers or synthesized oligomers. For some fragments, sequencing is performed after a series of deletions is made by exonuclease III digestion. The sequence is performed bidirectionally at least twice with either Sequenase (13) or by Taq polymerase (14). In some GC-rich areas, the sequence is performed using a gel containing 7% polyacrylamide, 8M urea, and 20% formamide.

Figure 1:
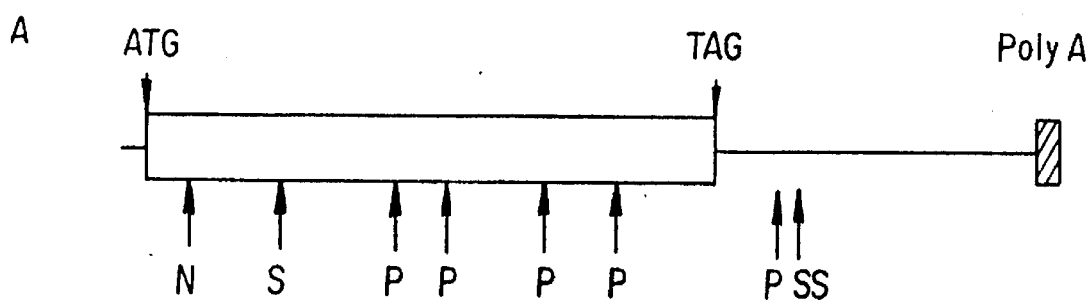
FIG. 1 depicts a partial restriction map and the cDNA clone of the cardiac adenylyl cyclase (B form).
Figure 1:
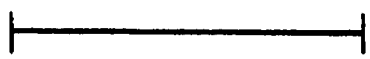
Figure 1:
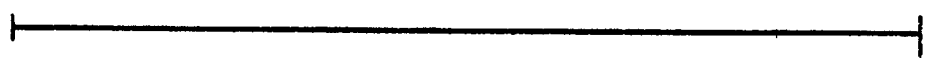

A clone designated #27 is found to be of particular interest. After the entire coding portion of clone #27 is sequenced, it is found that it contains an insert of 5.4 kb with a polyadenylation signal at its 3' end (FIG. 1). However, it does not contain an ATG with a conserved Kozak consensus sequence, which provides a favorable context for initiating translation (15).

A 5' EcoRI-SphI fragment from clone #27 is therefore used as a probe to rescreen the library. Several clones are obtained. It is found that a clone designated #6 overlaps for 800 bases with clone #27, and extends the cDNA sequence upstream an additional 441 bp. After sequencing the whole insert, an ATG with conserved Kozak consensus sequence is found at its 5' end (arrow, FIG. 1). This open reading frame of 3495 bases reads through to a TAG, a translation termination codon (FIGS. 1 and 2). Thus, clones #27 and #6 encode a protein of 1165 amino acids, which is 147 amino acids longer than the A form of cardiac adenylyl cyclase. The entire coding portion of the cDNA and its predicted amino acid sequence are shown (FIG. 2) (SEQ ID NO: 1).

A 4.0 kb EcoRI-SspI fragment from clones #6 (EcoRI-SphI) and #27 (SphI-SSpI) is subcloned into pcDNAamp (formed by introducing an ampicillin resistance gene into pcDNA1, obtained from Invitrogen). The resulting expression vector, containing the full length cDNA, is designated pcDNAamp/27-6. Samples of this expression vector, inserted into an appropriate E. coli strain designated DH5alpha, have been deposited with the American Type Culture Collection, 12301 Parklawn Drive, Rockville, Md. 20852, in accordance with the Budapest Treaty on the International Recognition of the Deposit of Microorganisms for the Purposes of Patent Procedure and have been accorded accession number ATCC 68826.

Production of this cardiac adenylyl cyclase is achieved by the cloning and expression of the cardiac adenylyl cyclase cDNA in a suitable expression system using established recombinant DNA methods. Production of the cardiac adenylyl cyclase can be achieved by incorporation of the cardiac adenylyl cyclase cDNA into any suitable expression vector and subsequent transformation of an appropriate host cell with the vector; alternatively, the transformation of the host cell can be achieved directly by naked DNA without the use of a vector. Production of the cardiac adenylyl cyclase by either eukaryotic cells or prokaryotic cells is contemplated by the present invention. Examples of suitable eukaryotic cells include mammalian cells, plant cells, yeast cells and insect cells. Similarly, suitable prokaryotic hosts, in addition to E. coli, include Bacillus subtilis.

Other suitable expression vectors may also be employed and are selected based upon the choice of host cell. For example, numerous vectors suitable for use in transforming bacterial cells are well known. For example, plasmids and bacteriophages, such as λ phage, are the most commonly used vectors for bacterial hosts, and for *E. coli* in particular. In both mammalian and insect cells, virus vectors are frequently used to obtain expression of exogenous DNA. In particular, mammalian cells are commonly transformed with SV40 or polyoma virus; and insect cells in culture may be transformed with baculovirus expression vectors. Yeast vector systems include yeast centromere plasmids, yeast episomal plasmids and yeast integrating plasmids.

It will also be understood that the practice of the invention is not limited to the use of the exact sequence of the cardiac adenylyl cyclase cDNA as defined in FIG. 2 (SEQ ID NO: 1). Modifications to the sequence, such as deletions, insertions, or substitutions in the sequence which produce silent changes in the resulting protein molecule are also contemplated. For example, alterations in the cDNA sequence which result in the production of a chemically equivalent amino acid at a given site are contemplated; thus, a codon for the amino acid alanine, a hydrophobic amino acid, can readily be substituted by a codon encodig another hydrophobic residue, such as glycine, or may be substituted with a more hydrophobic residue such as valine, leucine, or isoleucine. Similarly, changes which result in substitution of one negatively charged residue for another, such as aspartic acid for glutamic acid, or one positively charged residue for another, such as lysine for arginine, can also be expected to produce a biologically equivalent product.

Nucleotide changes which result in alteration of the N-terminal and C-terminal portions of the protein molecule frequently do not alter protein activity, as these regions are usually not involved in biological activity. It may also be desirable to eliminate one or more of the cysteines present in the sequence, as the presence of cysteines may result in the undesirable formation of multimere when the protein is produced recombinantly, thereby complicating the purification and crystallization processes.

Each of the proposed modifications is well within the routine skill in the art, as is determination or retention of biological activity of the encoded products. Therefore, where the phrase "cardiac adenylyl cyclase cDNA sequence" or "cardiac adenylyl cyclase gene" is used in either the specification or the claims, it will be understood to encompass all such modifications and variations which result in the production of a biologically equivalent cardiac adenylyl cyclase protein. It is also understood to include the corresponding sequence in other mammalian species. In particular, the invention contemplates those DNA sequences which are sufficiently duplicative of the sequence of FIG. 2 so as to permit hybridization therewith under standard high stringency Southern hybridization conditions, such a those described in Maniatis et al. (16).

In an example of such expression, twenty μg of the purified plasmid pcDNAamp/27-6 are transfected into the monkey kidney CMT cells using a modified method of Goolub et al. (17). Briefly, the cells are grown to 80% confluence in Dulbecco's modification of Eagle's Medium, 10% fetal calf serum, 2 mM glutamine, 4.5 mg/ml glucose, 10 μg/ml streptomycin sulfate and 60 μg/ml penicillin K. After washing with PBS twice, 0.5 ml of trypsin solution is added. The cells are incubated for 10 minutes, and 20 μg of purified plasmid resuspended in 4 ml of DMEM containing 400 μg/ml DEAE dextran and 0.1 mM chloroquine is added. The cell is incubated for four hours followed by 10% DMSO shock for two minutes. After washing with PBS twice, the induction media, which contains 10% fetal calf serum (FCS), 2 mM glutamine, 4.5 g/ml glucose, 2mM penicillin and streptomycin, and 1 μM $CdCl_2$, 0.1 μM $ZnCl_2$ in DMEM, is added. The plate is incubated at 37° C. for 72 hours before harvesting.

This adenylyl cyclase protein, composed of 1165 amino acids, is analyzed for secondary structure by the method of Kyte-Doolittle (11) (FIG. 3). The software, MacVector 3.5 (IBI, New Haven, Conn.), is used to obtain a hydropathy plot and thereby identify the membrane related structure of this cardiac adenylyl cyclase. The method of Kyte and Doolittle is used with a window size of 7.

As shown in FIG. 3, twelve peaks are numbered. These peaks represent transmembrane spanning regions. These results suggest that this cardiac adenylyl cyclase possesses a structure of twelve transmembrane spanning regions, as well as a large cytoplasmic loop located in the middle and at the end. In the transmembrane positions, the fifth extracellular loop is the largest (between the ninth and tenth transmembrane spans).

One hundred and fifty amino acids of the N-terminal tail are located in the cytoplasm, followed by a 6-transmembrane spanning region of 154 amino acids (amino acid position 151–304). Then 363 amino acids of the cytoplasmic domains (305–667) precede the second 6-transmembrane spanning domain of 242 amino acids (668–909), followed by another cytoplasmic domain of 256 amino acids (910–1165). Thus it makes a duplicated form of 6-transmembrane spanning region and large hydrophobic cytoplasmic domain.

As shown in FIG. 4, a DNA dot matrix comparison between the B form and the A form of cardiac adenylyl cyclase, the two large hydrophobic cytoplasmic loops show homology of 72–80% with each other. The homology between the two transmembrane spanning portions is also high (44–45%).

Thus, these two cardiac cyclases are clearly distinct from each other, but share much higher homology than with other types of cyclases, such as type I and type III. It is therefore reasonable to categorize these cardiac adenylyl cyclases as a new subclass of the entire adenylyl cyclase family. The only distinct difference between the two cardiac cyclases is that the A form lacks an N-terminal cytoplasmic domain, while the B form possesses such a domain 150 amino acids in length.

The membrane associated secondary structure of the protein (based on the results of FIG. 3) is well conserved among different types of mammalian adenylyl cyclases (types I, II, III, and cardiac types). All of them possess two large cytoplasmic loops, interrupted by the presence of 6-transmembrane spanning region. The homology among the different types of adenylyl cyclase is only conserved in the cytoplasmic portions, even though the other portions are structurally similar. Furthermore, in the same adenylyl cyclase protein the homology between the two cytoplasmic portions is also maintained. This suggests the cytoplasmic portion is a result of gene duplication.

It has been suggested that the level of activity of the adenylyl cyclases in the heart correlates with the development of heart failure. There is a significant decrease in the cyclase activity in the failed heart compared with that in the non-failed heart (10,18,19,20). These papers suggest that there is a distal regulation in the signal transduction pathway, i.e., the regulation at the level of cyclase. In fact, the decreased activity of adenylyl cyclase in the heart may be the major factor in the development of heart failure. Thus, the novel cardiac adenylyl cyclase of this invention is used to screen for compounds which stimulate the activity of that cyclase.

The biochemical property of this cardiac adenylyl cyclase is examined in a transient expression system using CMT cells (a derivative of COS cells). CMT cells contain T-antigen driven by a methalothionein promoter in the genome. Thus by induction with heavy metal ion in the medium, CMT cells could produce more T-antigen than COS cells. A 4.0 kb fragment of the adenylyl cyclase cDNA containing the whole coding sequence is inserted into the pcDNAamp plasmid described above.

The adenylyl cyclase activity of a membrane transfected with the expression vector pcDNAamp carrying cardiac adenylyl cyclase cDNA is assayed as follows. The transfected CMT cells are washed twice with PBS and scraped in three ml of cold buffer containing 50 mM Tris (pH 8.0), 1 mM EDTA, 10 μM PMSF (pheynlmethylsulfonylfluoride), 100 U leupeptin, and 50 U egg white trypsin inhibitor (ETI) on ice. The membrane is homogenated in Polytron™ (setting 6 for 10 seconds) and is centrifuged at 800×g for 10 minutes at 4° C. The supernatant is further centrifuged at 100×g for 40 minutes at 4° C. The resultant pellet is resuspended in 50 mM Tris (pH 8.0), 1 mM EDTA, 1 μM PMSF, 50 U leupeptin, and 50 U ETI, to a concentration of 5 μg/μl. This crude membrane solution is used for the adenylyl cyclase asssay.

The adenylyl cyclase assay is performed by the method of Salomon (21). Briefly, the crude membranes from CMT cells are resuspended in a solution containing 1 mM creatine phosphate, 8 μg/ml creatine phophokinase, 4 mM HEPES (pH 8.0), 2 mM $MgCl_2$, 0.1 mM c-AMP, 0.1 mM ATP, and $^{32}P$-ATP (0.2–5 μCi/assay tube). The reaction mixture is incubated at 37° C. for 30 minutes and the reaction is stopped by the addition of 100 μl 2% sodium dauryl sulfate. To monitor the recovery from the column, 3H-labelled c-AMP is used. Cyclic-AMP is separated from ATP by passing through Dowex and alumina columns, and the radioactivity is counted by scintillation counter. The protein concentrations of the membranes used are measured by Bradford's method (22), with bovine serum albumin as a standard.

The membrane from untransfected CMT cells is used as a control. The results of the adenylyl cyclase activity assay are shown in Table 1:

TABLE 1

|  | Basal* | NaF* | GTPγS* | Forskolin* |
| --- | --- | --- | --- | --- |
| Control | 4 ± 0.7 | 17 ± 3 | 30 ± 5 | 61 ± 11 |
| Transfected | 9 ± 1 | 46 ± 5 | 114 ± 12 | 223 ± 27 |

*control < transfected, p < 0.05, control (n = 6), transfected (n = 8)

The adenylyl cyclase expressed by this cDNA is well stimulated by 10 mM sodium fluoride, 100 μM GTPγS and 100 μM forskolin. It shows 2.7, 3.8 and 3.7 fold more stimulation than the control. Values are shown with ± standard error.

An increased basal activity of adenylyl cyclase in the transfected cells is also observed. This suggests that this cyclase possesses high basal activity, allowing high accumulation of cyclic AMP in the heart. This is consistent with the high basal cyclase activity seen in cardiac tissue.

In order to clarify the tissue distribution of the cardiac adenylyl cyclase (B form), Northern blotting is performed using mRNA from various tissues. Messenger RNA is purified using guanidium sodium (20) and oligo-dT columns from various canine tissues (heart, brain, testis, skeletal muscle, kidney and lung). Five μg of mRNA are used for each assay (per lane of blot).

The blot is prehybridized in a solution containing 50% formamide, 5×SSC, 5×Denhardt's, 25 mM $NaPO_4$ (pH 6.5), 0.25 mg/ml calf thymus DNA, and 0.1% SDS at 42° C. for two hours before the addition of a probe. The entire 5.4 kb cDNA fragment from the adenylyl cyclase cDNA clone #27 is used as a probe. The probe is made by a multiprimer random labelling method with $^{32}P$-dCTP. Hybridization is performed at 42° C. for 18 hours followed by washing under increasingly stringent conditions. The blot is then autoradiographed.

The results of the Northern blot analysis, as depicted in FIG. 5, show that the message is most abundant in the heart, as well as in the brain, but much less expressed in other tissues, such as testis, skeletal muscle, kidney and lung.

The single class of message which hybridizes with a fragment from clone #27 is 6 kb in size, clearly distinct from the messages (5 and 7 kb) with clone #113 which contains the cDNA for the A form of the cyclase.

BIBLIOGRAPHY

1. Salter, R. S., et al., *J. Biol. Chem.*, 256, 9830–9833 (1981).

2. Pfeuffer E., et al., *EMBO J.*, 4, 3675–3679 (1985).

3. Mollner, S., et al., *Eur. J. Biochem.*, 195, 281–286 (1991).

4. Livingstone, M. S., et al., *Cell*, 37, 205–215 (1984).

5. Krupinski, J., et al., *Science*, 244, 1558–1564 (1989).

6. Tang, W-T, et al., *J. Biol. Chem.*, 266, 8595–8603 (1991).

7. Bakalyar, H. A., and Reed, R. R., *Science*, 250, 1403–1406 (1990).

8. Pfeuffer, E., et al., *Proc. Natl. Acad. Sci. USA.*, 82, 3086–3090 (1985).

9. Mollner, S., and Pfeuffer, T., *Eur. J. Biochem.*, 171, 265–271 (1988).

10. Chen, L., et al., *J. Clin. Invest.*, 87, 293–298 (1991).

11. Kyte, J., and Doolittle, R. F., *J. Mol. Biol.*, 157, 105–132 (1982).

12. Watson, C. J. and Jackson, J. F., in *DNA Cloning: A Practical Approach*, Glover, D. M., ed., vol. 1, pp.79–88 (1985).

13. Tabor, S., and Richardson, C. C., *Proc. Natl. Acad. Sci. USA*, 84, 4767–4771 (1987).

14. Innis, M. A., et al., *Proc. Natl. Acad. Sci. USA*, 85, 9436–9440 (1988).

15. Kozak, M., *J. Cell. Biol.*, 108, 229–241 (1989).

16. Maniatis et al., *Molecular Cloning: A LabOratory Manual*, Cold Spring Harbor Laboratory, (1982).

17. Goolub, E. I., et al., *Nucleic Acid Research*, 17, 4902 (1989).

18. Robberecht, P., et al., *Biochem. Pharmacol*, 30, 385–387 (1981).

19. Chatelain, P., et al., *Eur. J. Pharmacol.*, 72, 17–25 (1981).

20. Palmer, G. C., and Greenberg, S., *Pharmacology*, 19, 156–162 (1979).

21. Salomon, Y., *Adv. Cyclic Nucleotide Res.*, 10, 35–55 (1979).

22. Bradford, M., *Anal. Blochem.*, 73, 248 (1976).

23. Chomczynski, P., and Sacchi, N., *Anal. Biochem.*, 162, 156–159 (1987).

What is claimed is:

1. A purified and isolated cardiac adenylyl cyclase which has the amino acid sequence depicted in FIG. 2. and identified as SEQ ID NO: 2.

* * * * *